(12) United States Patent
Djupesland

(10) Patent No.: US 7,347,201 B2
(45) Date of Patent: Mar. 25, 2008

(54) NASAL DELIVERY DEVICES

(75) Inventor: Per Gisle Djupesland, Oslo (NO)

(73) Assignee: Optinose AS, Olso (NO)

( * ) Notice: Subject to any disclaimer, the term of this patent is extended or adjusted under 35 U.S.C. 154(b) by 225 days.

(21) Appl. No.: 10/469,114

(22) PCT Filed: Feb. 26, 2002

(86) PCT No.: PCT/IB02/01612

§ 371 (c)(1), (2), (4) Date: Feb. 12, 2004

(87) PCT Pub. No.: WO02/068031

PCT Pub. Date: Sep. 6, 2002

(65) Prior Publication Data

US 2004/0112380 A1    Jun. 17, 2004

Related U.S. Application Data

(63) Continuation-in-part of application No. 09/700,532, filed on Nov. 15, 2000, now Pat. No. 6,715,485.

(30) Foreign Application Priority Data

Mar. 3, 1999 (GB) .................................. 9904906.6
May 19, 1999 (GB) .................................. 9911686.5
Feb. 26, 2001 (GB) .................................. 0104692.9

(51) Int. Cl.
  *A61M 11/00* (2006.01)
  *A61M 15/00* (2006.01)

(52) U.S. Cl. .............................. 128/200.23; 128/203.15

(58) Field of Classification Search ........... 128/200.13, 128/200.14, 200.21, 200.22, 200.23, 203.12, 128/203.13, 203.15, 203.16, 203.18, 203.22, 128/203.23, 203.24, 203.26, 203.27, 203.29, 128/204.12, 206.11, 206.29, 207.18, 206.17
See application file for complete search history.

(56) References Cited

U.S. PATENT DOCUMENTS

| 3,302,374 | A | * | 2/1967 | Szekely | ....................... 96/260 |
| 5,080,093 | A | * | 1/1992 | Raabe et al. | ........... 128/203.12 |
| 5,479,920 | A | * | 1/1996 | Piper et al. | ............ 128/204.23 |
| 5,584,285 | A |   | 12/1996 | Salter et al. | |
| 5,617,844 | A | * | 4/1997 | King | ..................... 128/200.18 |

(Continued)

FOREIGN PATENT DOCUMENTS

DE          40 15 367          11/1991

(Continued)

*Primary Examiner*—Teena Mitchell
(74) *Attorney, Agent, or Firm*—Proskauer Rose LLP; Kristin H. Neuman, Esq.

(57) ABSTRACT

An exhalation breath-actuated nasal delivery device for and a method of delivering a substance to a nasal cavity of a subject, the delivery device comprising: a nosepiece (40) for fitting to a nostril of a subject; a mouthpiece (42) through which the subject in use exhales; and delivery unit (64), as one of a mechanical delivery pump (66) or a nebulizer (115), for delivering a substance to the nosepiece (40); and an actuation mechanism (74) for actuating the delivery unit in response to oral exhalation through the mouthpiece, and preferably when at least one or both of the pressure at or the flow rate through the nosepiece exceeds a predetermined threshold.

36 Claims, 6 Drawing Sheets

U.S. PATENT DOCUMENTS

| | | | | |
|---|---|---|---|---|
| 6,138,668 A | * | 10/2000 | Patton et al. | 128/200.14 |
| 6,269,810 B1 | * | 8/2001 | Brooker et al. | 128/203.12 |
| 6,422,234 B1 | * | 7/2002 | Bacon | 128/200.14 |
| 6,450,163 B1 | * | 9/2002 | Blacker et al. | 128/200.18 |
| 6,557,549 B2 | * | 5/2003 | Schmidt et al. | 128/200.24 |
| 6,612,303 B1 | * | 9/2003 | Grychowski et al. | 128/200.21 |
| 6,681,767 B1 | * | 1/2004 | Patton et al. | 128/203.15 |
| 6,715,485 B1 | * | 4/2004 | Djupesland | 128/203.15 |
| 6,732,731 B1 | * | 5/2004 | Tseng | 128/200.21 |
| 6,929,003 B2 | * | 8/2005 | Blacker et al. | 128/203.12 |
| 2004/0050385 A1 | * | 3/2004 | Bonney et al. | 128/203.15 |
| 2004/0089299 A1 | * | 5/2004 | Bonney et al. | 128/203.15 |
| 2005/0217666 A1 | * | 10/2005 | Fink et al. | 128/200.14 |

FOREIGN PATENT DOCUMENTS

| | | |
|---|---|---|
| WO | 93/18812 | 9/1993 |
| WO | 97/31721 | 9/1997 |
| WO | 98/03267 | 1/1998 |
| WO | 98/53869 | 12/1998 |
| WO | 00/35523 | 6/2000 |
| WO | 00/51672 | 9/2000 |

* cited by examiner

NASAL DELIVERY DEVICES

RELATED APPLICATIONS

This application is a national phase of International Application No. PCT/IB02/01612 filed Feb. 26, 2002 and published in the English language, and a continuation-in-part of U.S. patent application Ser. No. 09/700,532 filed Nov. 15, 2000 now U.S. Pat. No. 6,715,485, which is hereby incorporated herein by reference in its entirety.

FIELD OF THE INVENTION

The present invention relates to a nasal delivery device for and a method of delivering a substance, in particular one of a liquid, as a suspension or solution, or a powder containing a medicament, especially systemic or topical pharmaceuticals, a cleansing agent, or an irrigating agent, as a liquid, preferably combined with a cleansing agent, to the nasal airway of a subject. In particular, the present invention relates to an oral exhalation breath-actuated nasal delivery device including a mechanical nasal delivery pump for delivering a substance to the nasal airway of a subject, and an oral exhalation breath-actuated nasal delivery device including a nebulizer for delivering a substance to the nasal airway of a subject.

BACKGROUND AND SUMMARY OF THE INVENTION

Referring to FIG. 1, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficiency delivery. Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse affects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as helicobacter pylori infections which cause gastric ulcers.

To date, nasal medicaments have been primarily delivered as drops or by mechanical nasal spray pumps. With mechanical spray pumps, the mean particle size is typically between 40 μm and 80 μm in order to prevent the inhalation of delivered particles. In general, particles smaller than 10 μm will bypass the nose and can be inhaled. Indeed, the new FDA guidelines require that the fraction of particles less than 10 μm be at most 5%.

Whilst the provision of a spray having a larger mean particle size prevents the inhalation of the particles, these larger particles are not optimal for achieving a good distribution to the nasal mucosa.

The applicant has now recognized that the closure of the oropharyngeal velum during the delivery of a substance to the nasal airway prevents the possible inhalation of the substance, thereby enabling the delivery of an aerosol having a much smaller mean particle size than achieved by traditional nasal spray pumps. In this way, an aerosol can be generated which has an optimal particle size distribution.

A further advantage is that the nosepiece acts to expand the narrowest, anterior part of the nasal cavity and thereby reduces the unwanted high deposition in the anterior region of the nasal cavity which is lined by squamous epithelium.

In addition, the applicant has recognized that, by establishing a bidirectional flow through the nasal cavities as described in WO-A-00/51672, that is, an air flow which passes into one nostril, around the posterior margin of the nasal septum and in the opposite direction out of the other nostril, an aerosol having an optimal flow rate and timing can be generated. Furthermore, the bidirectional air flow advantageously acts to stimulate the sensory nerves in the nasal mucosa, thereby conditioning the subject for the delivery and providing a more comfortable delivery situation.

A yet further advantage is that the air flow acts to create a positive pressure inside the nasal passages connected in series, which tends to expand and widen narrow and congested regions.

A still yet further advantage is that the two-point fixation of the device in the nose with a well-fitting nozzle and in the mouth provides a much more stable and reproducible positioning of the device as compared to traditional spray pumps. Thus, in addition to improved deposition and reproducibility, the new concept provides a more user-friendly and intuitive nasal delivery method.

Furthermore, the delivery device, in being pre-primed and actuatable by the oral exhalation breath of a subject, does not require the application of an actuation force by the subject at the time of actuation. Traditionally, mechanical liquid delivery pumps are operated by the manual compression of a chamber containing a volume of liquid to expel a flow of a metered volume of liquid, and mechanical powder delivery pumps are operated by the manual compression of a chamber containing a volume of air to drive and expel a flow of a metered amount of a dry powder. Such operation requires a relatively high actuation force, typically of the order of 50 N, which high force often leads to significant movement of the delivery device, it being very difficult to maintain a delivery device stationary when attempting to apply a high actuation force. Movement of the delivery device, both in the positioning and orientation of the nozzle, will lead to poor reproducibility, dose accuracy and patient compliance. In being pre-primed and actuatable by the oral exhalation breath of a subject, the delivery device of the present invention overcomes this problem.

In addition, by not requiring a subject to apply an actuation force at the instance of delivery, the delivery device provides for the same actuation force in each delivery, and also provides for delivery at an optimal pressure and/or flow rate, and the delivery of substance having an optimized particle size distribution.

Yet furthermore, in providing for the closure of the oropharyngeal velum of a subject, substance is prevented from entering the lower airway, and also, in a preferred embodiment, bi-directional delivery can be achieved through the nasal cavities.

It will be appreciated that the nasal delivery devices of the present invention are quite different to inhalation devices which provide for inhalation into the lower airway.

Inhalation devices have been used for a long time for the inhalation of medicaments in the treatment of lower airway pathologies.

One such inhalation device is the pressurized metered dose inhaler (pMDI). In such inhalers, a metered dose of medicament is released as an aerosol by actuating an aerosol canister, with the particle sizes of the aerosol being required to be small, typically less than 5 μm, in order to reach the distal parts of the lower airway. One drawback with traditional pMDIs is that the subject must co-ordinate inhalation with the aerosol release in order to deliver the aerosolized medicament effectively to the lower airway. Inadequate co-ordination represents a considerable problem, significantly reducing both lung deposition and reproducibility. Another drawback with traditional pMDIs is the use of chlorine-containing compounds as the propellant gas, as such gases are not environmentally friendly and have been demonstrated to destroy the ozone layer. Recently, in order to alleviate these drawbacks, pMDIs have been developed which use an alternative propellant gas, this being a hydrofluoroalkane (HFA), and incorporate a breath-actuation mechanism which provides for actuation of the aerosol canister on inhalation by the subject.

Another such inhalation device is the dry powder inhaler, such as the Turbohaler® inhaler as supplied by AstraZeneca and the Discus® inhaler as supplied by GSK. These dry powder inhalers do not require co-ordination of delivery and inhalation and can improve deposition to the lower airways.

Bi-directional nasal drug delivery is achieved by directing an exhaled air flow through the nasal passages in series, or by triggering another flow source to create such an air flow, whereas breath actuation of pulmonary drug delivery is by inhalation into a closed expanding volume, that is, the lungs. For bi-directional nasal delivery, it is desirable to establish the air flow before the drug is released, whereas for inhalation, the release is best achieved at the very beginning of inspiration to reach the most distal parts of the lungs.

Increased airway resistance in pathological conditions, both in the pulmonary and nasal airways, is a challenge. In inhalation devices, an air flow is created by the inspiratory muscles creating a negative pressure inside the chest. In this way, air is sucked through the device and into the airways. For pulmonary drug delivery, it is essential that the triggering occurs, not only early, but also at a relatively low flow to ensure release in subjects with a very low lung capacity. Furthermore, the releasing action should require as little energy as possible, as any resistance in the device will impede free inhalation. Still most subjects, even patients with lung diseases, will be able to achieve a flow rate of 25 L/min which is typically required to trigger the release from a pMDI device.

For the nose, the situation is more complex and in many ways different. The expiratory muscles in the thorax produce the exhaled air flow used to trigger release, and this air flow is then directed through the device and into the nasal passages in series, or used to trigger another flow source. Thus, the triggering air flow is completely reversed as compared to pulmonary breath actuation, and the air flow is directed into another airway/compartment separated from the lower airways.

Furthermore, the nose geometry is designed to humidify, warm and filter the inspired air to protect the lower airways. The resistance in the nose alone equals 50% of the total airway resistance, and the resistance may increase immensely when congested. Owing to the high anterior resistance, turbulence occurs just posterior to the constriction, increasing deposition in this region. To achieve a better distribution to larger and more posterior parts of the nasal mucosa, it is envisaged to be advantageous to have the drug released at a lower flow in a congested nose and at a higher flow in an open nose. This requires a system which can be released not only by flow, but also by pressure. Such release is essential for efficient and reliable exhalation-triggered nasal drug delivery. The two main triggering modes, flow and pressure, are to certain extent overlapping. They can be incorporated in one single mechanism or provided as separate mechanisms. However, the nose may become completely blocked, in particular during colds and allergic attacks. In this situation, it becomes impossible to establish a bi-directional air flow, but still it is desirable and necessary to deliver drugs to the nose.

In one aspect the present invention provides a nasal delivery device for delivering a substance to a nasal cavity of a subject, comprising: a nosepiece for fitting to a nostril of a subject; a mouthpiece through which the subject in use exhales; a nozzle for directing a substance through the nosepiece; a mechanical delivery pump fluidly connected to the nozzle for delivering a substance to the nozzle; and an actuation mechanism for actuating the mechanical delivery pump in response to oral exhalation through the mouthpiece.

In one embodiment the actuation mechanism includes a trigger mechanism for actuating the delivery pump at a predeterminable pressure.

In another embodiment the actuation mechanism includes a trigger mechanism for actuating the delivery pump at a predeterminable flow rate.

In a further embodiment the actuation mechanism includes a trigger mechanism for actuating the delivery pump at one or both of a predeterminable pressure and a predeterminable flow rate.

In one embodiment the delivery device further comprises: a flow channel fluidly connecting the nosepiece and the mouthpiece, whereby exhaled air from an exhalation breath is in use delivered through the nosepiece.

In another embodiment the delivery device further comprises: a flow channel fluidly connected to the nosepiece through which a gas flow, separate to an exhaled air flow from an exhalation breath of the subject, is in use delivered; and a gas supply unit for supplying a gas flow to the flow channel.

Preferably, the gas supply unit is configured to be actuated by exhalation through the mouthpiece.

In one embodiment the delivery pump comprises a liquid delivery pump for delivering a metered volume of a liquid.

In another embodiment the delivery pump comprises a powder delivery pump for delivering a metered amount of a powder.

In one embodiment the nozzle is configured to deliver an aerosol.

In another embodiment the nozzle is configured to deliver a jet.

In another aspect the present invention provides an oral exhalation breath-actuated mechanical nasal delivery pump unit for delivering a substance to a nasal cavity of a subject, the pump unit including an outlet nozzle and a mechanical delivery pump.

In one embodiment the delivery pump comprises a liquid delivery pump for delivering a metered volume of a liquid.

In another embodiment the delivery pump comprises a powder delivery pump for delivering a metered amount of a powder.

In one embodiment the nozzle is configured to deliver an aerosol.

In another embodiment the nozzle is configured to deliver a jet.

In a further aspect the present invention provides a method of delivering a substance to a nasal cavity of a subject, comprising the steps of: providing a nasal delivery device to the nasal cavity of a subject, the delivery device including a nosepiece for fitting to a nostril of the subject, a mouthpiece through which the subject exhales, a nozzle for directing a substance through the nosepiece, and a mechanical delivery pump fluidly connected to the nozzle for delivering a substance to the nozzle; and actuating the delivery pump in response to oral exhalation through the mouthpiece to deliver a substance through the nosepiece.

In one embodiment the step of actuating the delivery pump comprises the step of: actuating the delivery pump in response to oral exhalation through the mouthpiece on generation of a predeterminable pressure at the nosepiece.

In another embodiment the step of actuating the delivery pump comprises the step of: actuating the delivery pump in response to oral exhalation through the mouthpiece on generation of a predeterminable flow rate through the nosepiece.

In a further embodiment the step of actuating the delivery pump comprises the step of: actuating the delivery pump in response to oral exhalation through the mouthpiece on generation of one or both of a predeterminable pressure at or a predeterminable flow rate through the nosepiece.

In one embodiment the delivery device further comprises a flow channel fluidly connecting the nosepiece and the mouthpiece, whereby exhaled air from an exhalation breath is delivered through the nosepiece.

In another embodiment the method further comprises the step of: delivering a gas flow, separate to an exhaled air flow from an exhalation breath of the subject, through the nosepiece.

In one embodiment the delivery pump comprises a liquid delivery pump for delivering a metered volume of a liquid.

In another embodiment the delivery pump comprises a powder delivery pump for delivering a metered amount of a powder.

In one embodiment the substance is delivered as an aerosol.

In another embodiment the substance is delivered as a jet.

In a yet further aspect the present invention provides a method of delivering a substance to a nasal cavity of a subject, comprising the step of actuating a mechanical nasal delivery pump unit, the pump unit including an outlet nozzle and a mechanical delivery pump fluidly connected thereto, on oral exhalation by the subject to deliver a substance to a nasal cavity of the subject.

In one embodiment the delivery pump comprises a liquid delivery pump for delivering a metered volume of a liquid.

In another embodiment the delivery pump comprises a powder delivery pump for delivering a metered amount of a powder.

In one embodiment the substance is delivered as an aerosol.

In another embodiment the substance is delivered as a jet.

In a still further aspect the present invention provides an exhalation breath-actuated nasal delivery device for delivering a substance to a nasal cavity of a subject, comprising: a nosepiece for fitting to a nostril of a subject; a mouthpiece through which the subject in use exhales; a nebulizer for delivering an aerosol including a substance to the nosepiece; and an actuation unit for actuating the nebulizer when at least one or both of the pressure at or the flow rate through the nosepiece exceeds a predetermined threshold in response to oral exhalation through the mouthpiece.

In one embodiment the delivery device further comprises: a flow channel fluidly connecting the nosepiece and the mouthpiece, whereby exhaled air from an exhalation breath is in use delivered through the nosepiece.

Preferably, the actuation unit includes a flow regulator for regulating a flow of exhaled air from an exhalation breath.

In another embodiment the delivery device further comprises: a flow channel fluidly connected to the nosepiece through which a gas flow, separate to an exhaled air flow from an exhalation breath of the subject, is in use delivered; and a gas supply unit for supplying a gas flow to the flow channel.

Preferably, the gas supply unit is configured to be actuated by exhalation through the mouthpiece.

In one embodiment the nebulizer comprises an ultrasonic nebulizer.

In another embodiment the nebulizer comprises a flow-generated nebulizer.

In a further embodiment the nebulizer comprises an electrohydrodynamic nebulizer.

In yet another aspect the present invention provides a breath-actuated nasal delivery device, comprising: a flow channel including a mouthpiece through which a subject in use exhales and a nosepiece for fitting to one nostril of the subject and through which an exhaled air flow is in use delivered to the nostril of the subject; a nebulizer for delivering an aerosol including a substance to the flow channel; and a trigger mechanism for actuating the nebulizer when the pressure and/or flow of the air exhaled through the mouthpiece exceeds a predeterminable threshold.

In a still yet further aspect the present invention provides a method of delivering a substance to a nasal cavity of a subject, comprising the steps of: providing a nasal delivery device comprising a nosepiece for fitting to a nostril of a subject, a mouthpiece through which the subject exhales, and a nebulizer for delivering an aerosol including a substance to the nosepiece; and actuating the nebulizer when at least one or both of the pressure at or the flow rate through the nosepiece exceeds a predetermined threshold in response to oral exhalation through the mouthpiece.

In one embodiment the delivery device further comprises a flow channel fluidly connecting the nosepiece and the mouthpiece, whereby exhaled air from an exhalation breath is delivered through the nosepiece.

Preferably, the delivery device further comprises a flow regulator for regulating a flow of exhaled air from an exhalation breath.

In another embodiment the method further comprises the step of: delivering a gas flow, separate to an exhaled air flow from an exhalation breath of the subject, through the nosepiece.

In one embodiment the nebulizer comprises an ultrasonic nebulizer.

In another embodiment the nebulizer comprises a flow-generated nebulizer.

In a further embodiment the nebulizer comprises an electrohydrodynamic nebulizer.

BRIEF DESCRIPTION OF THE DRAWINGS

Preferred embodiments of the present invention will now be described hereinbelow by way of example only with reference to the accompanying drawings, in which.

DETAILED DESCRIPTION

Figure 1:
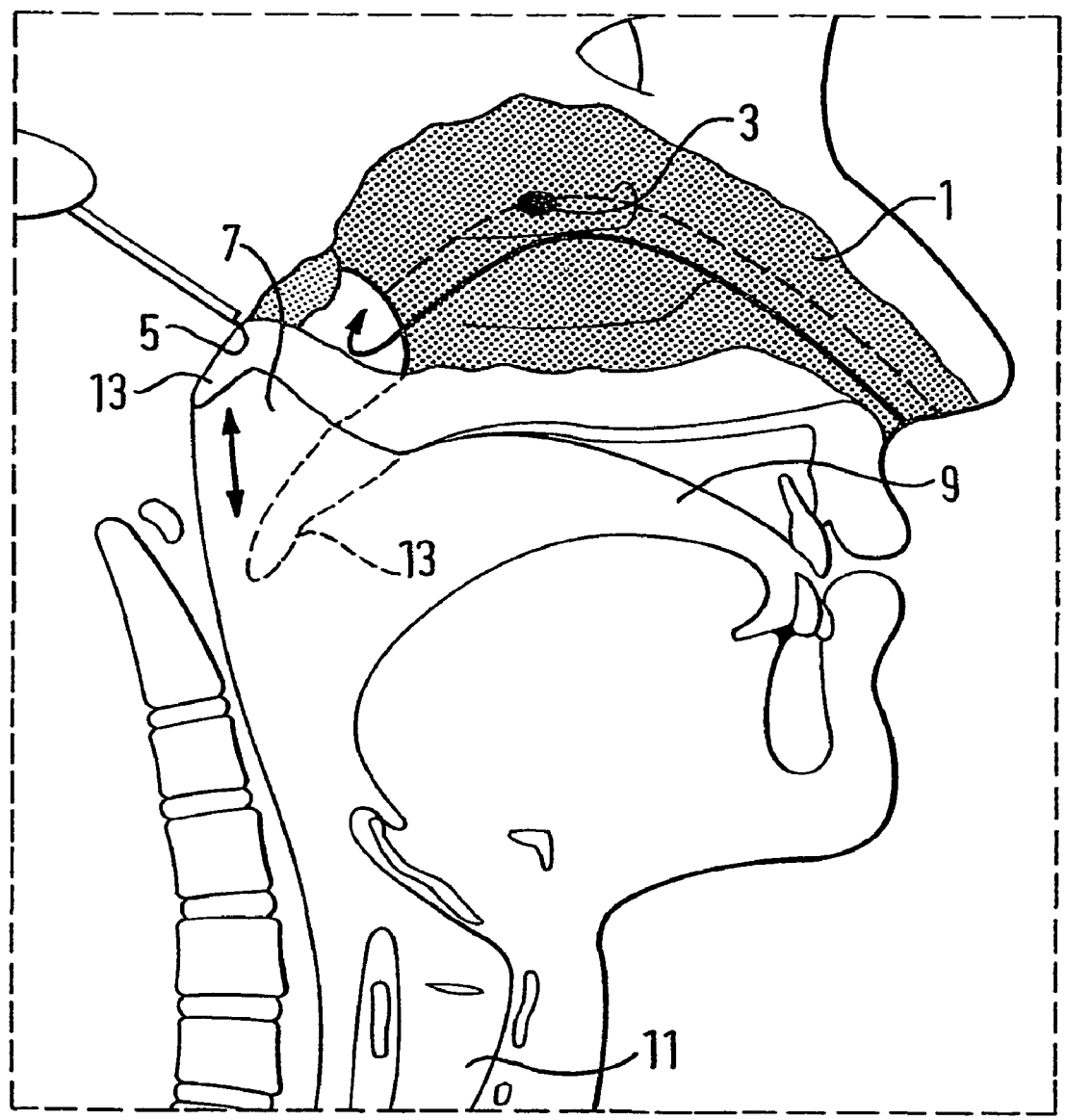
FIG. 1 diagrammatically illustrates the upper airway of a human subject.
Figure 2A:
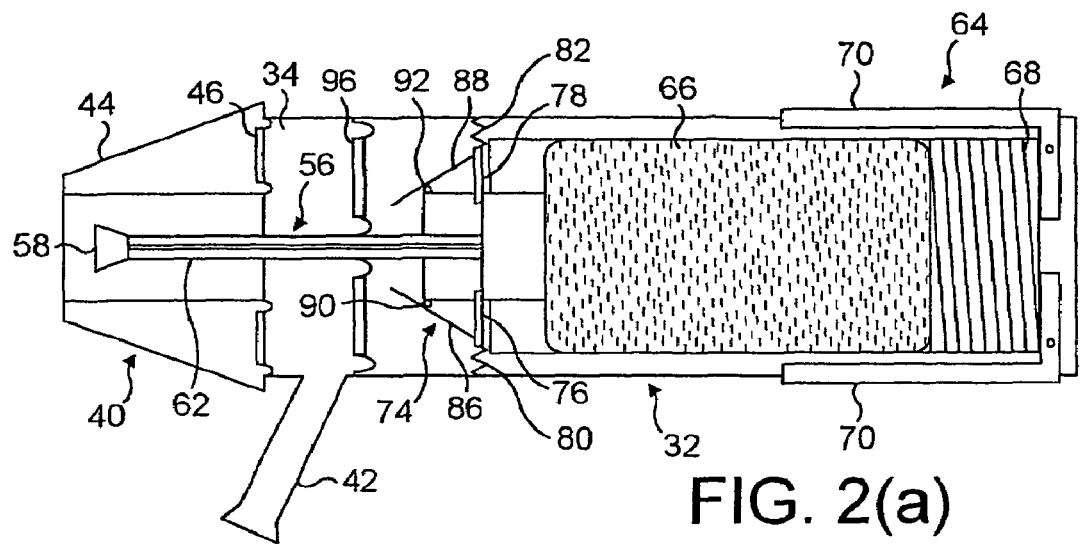
FIGS. 2(a) to (d) illustrate an exhalation breath-actuated nasal delivery device in accordance with a first embodiment of the present invention.
Figure 2B:
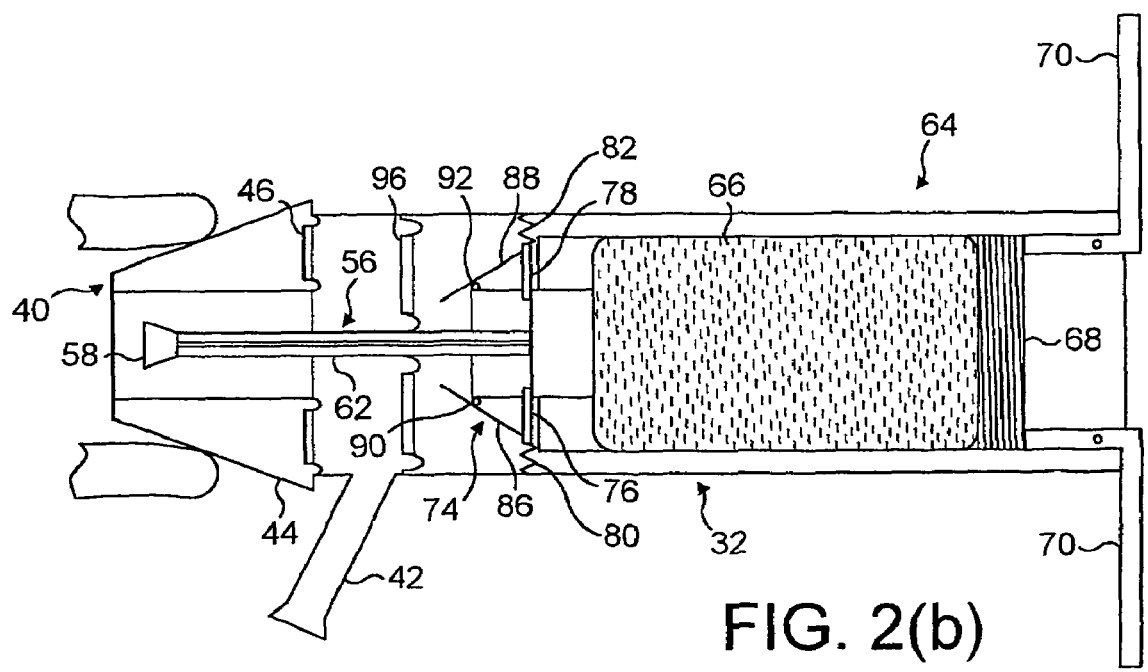
Figure 2C:
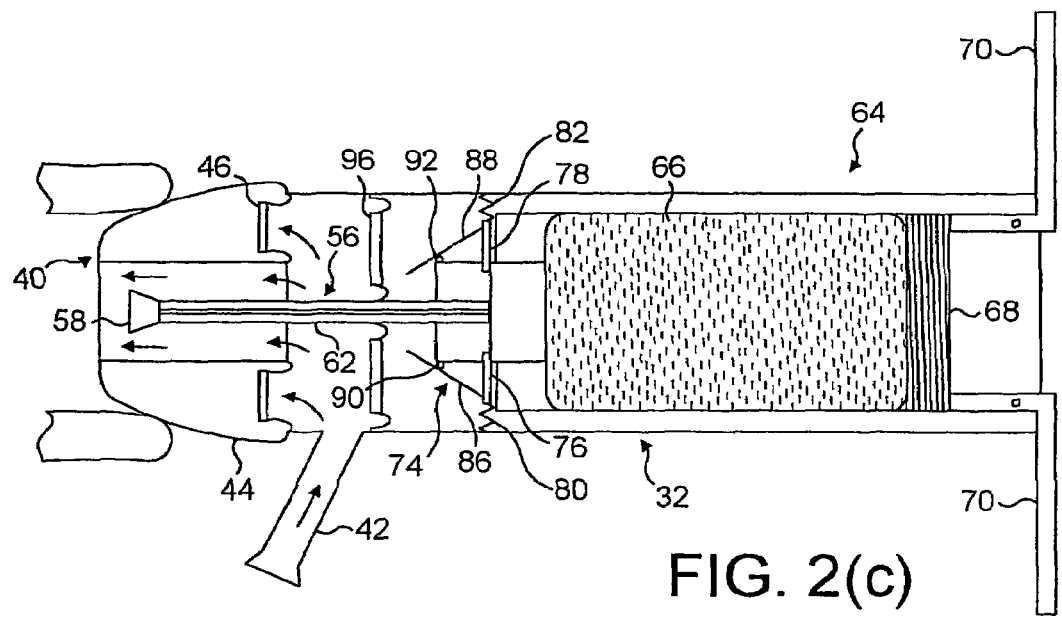
Figure 2D:
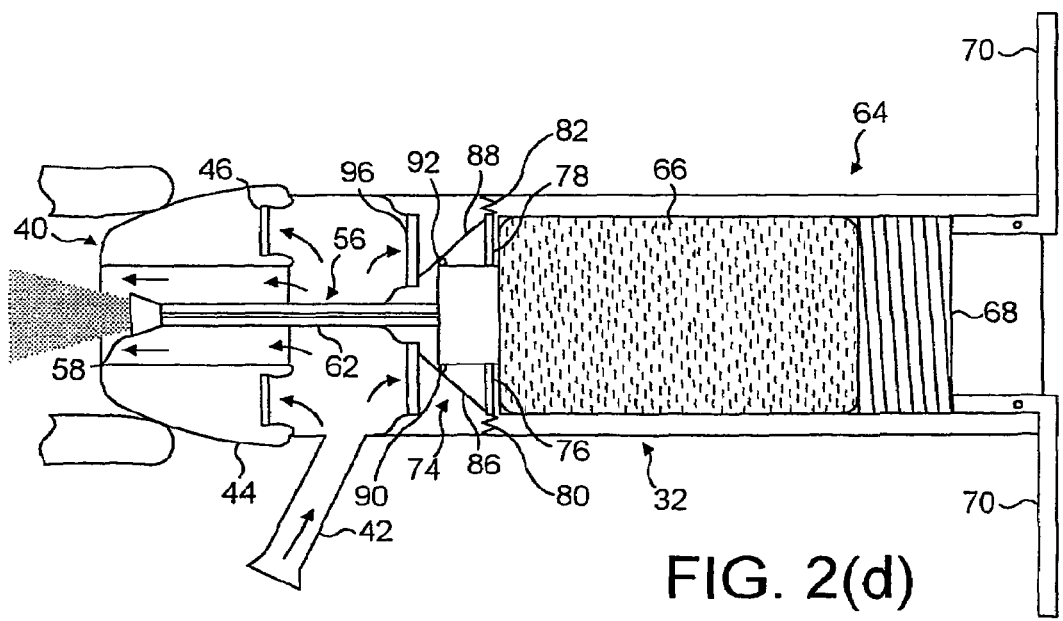
Figure 3A:
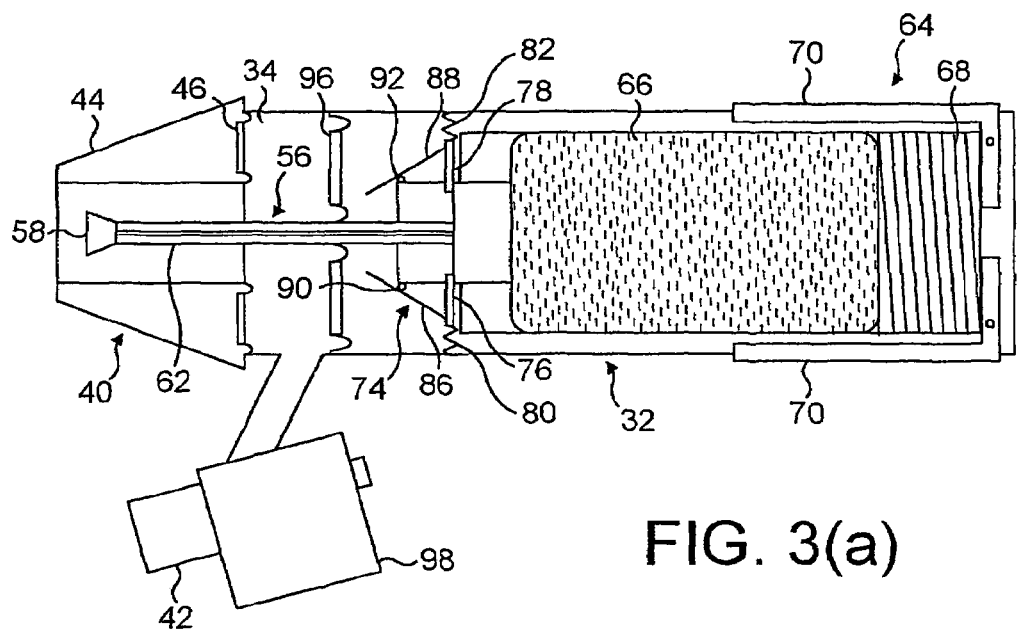
FIGS. 3(a) to (d) illustrate an exhalation breath-actuated nasal delivery device in accordance with a second embodiment of the present invention.
Figure 3B:
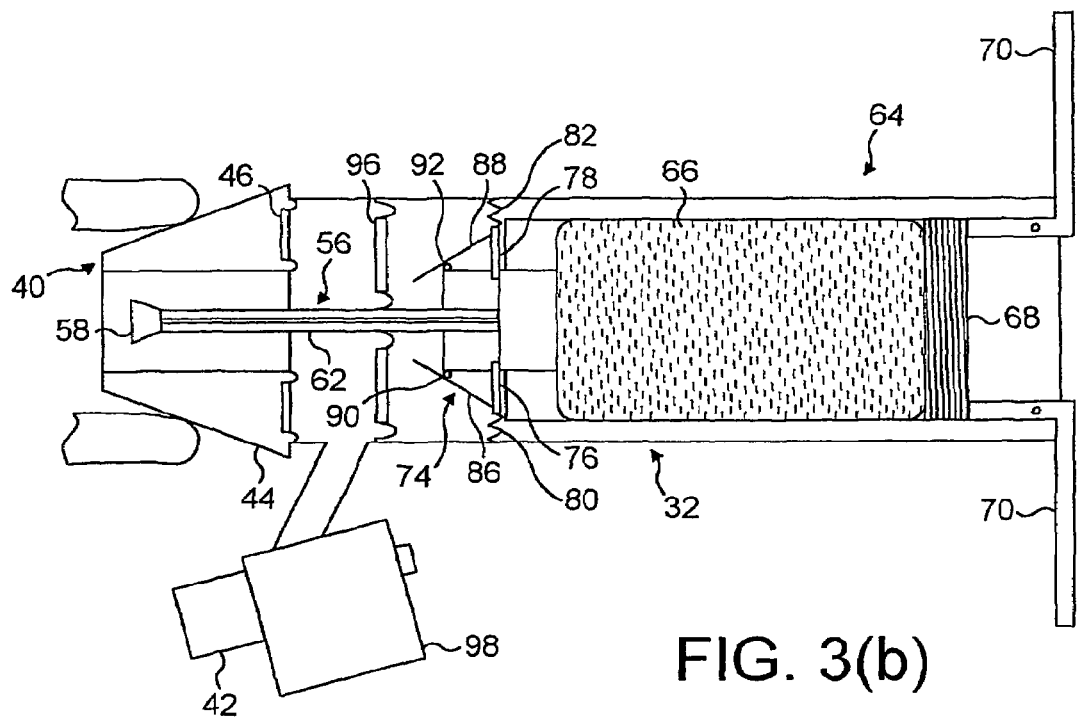
Figure 3C:
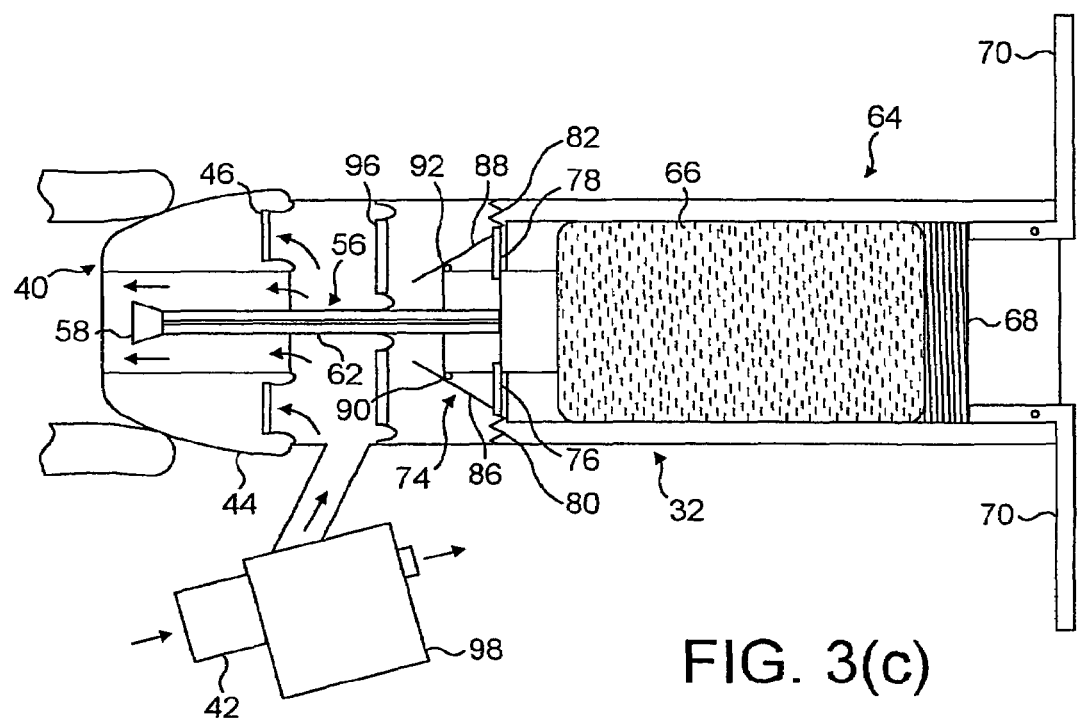
Figure 3D:
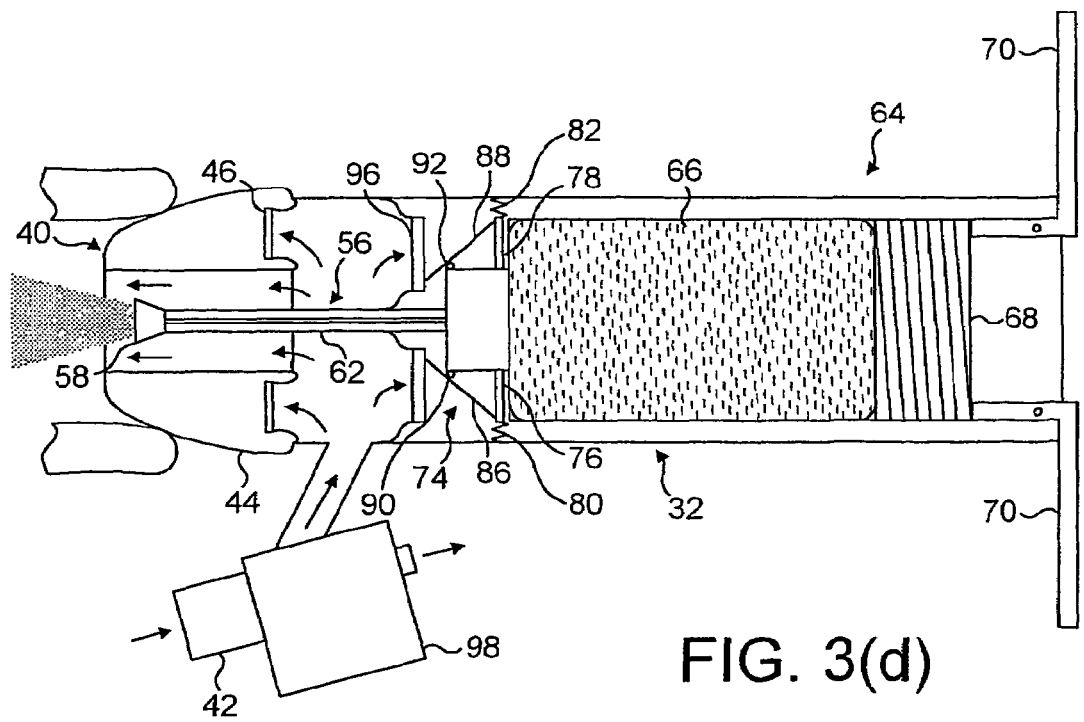

FIGS. 2(a) to (d) illustrate an oral exhalation breath-actuated nasal delivery device in accordance with a first embodiment of the present invention.

The delivery device comprises a housing 32 which includes a chamber 34 for receiving the exhalation breath of a subject, a nosepiece 40 for fitting in a nostril of the subject which is in fluid communication with the chamber 34 in the housing 32 and disposed to one, the distal, end of the housing 32, and a mouthpiece 42 through which the subject exhales and which is in fluid communication with the chamber 34 in the housing 32.

The nosepiece 40 is an expandable member which is configured to expand on exhalation through the mouthpiece 42 such as to promote a sealing fit between the nosepiece 40 and a nostril of a subject, with such a sealing fit only being achievable on the nosepiece 40 firstly being sufficiently inserted into the nostril of the subject for effective operation of the delivery device. Where the nosepiece 40 is not sufficiently inserted into a nostril of a subject for effective operation of the delivery device, exhaled air from the exhalation breath of the subject escapes to the atmosphere between the outer peripheral surface of the nosepiece 40 and the nostril of the subject. In this embodiment the nosepiece 40 comprises an enclosed, gas-filled annular member, the outer surface 44 and at least a part of the inner surface 46 of which are flexible elements, in this embodiment resilient elements, such that the pressure generated in the chamber 34 in the housing 32 by the exhalation breath of a subject acts on the flexible inner surface 46 of the nosepiece 40 to cause the flexible outer surface 44 of the nosepiece 40 to expand outwardly into contact with the nostril of the subject, and thereby both seal the nosepiece 40 to the nostril of the subject and expand the nostril, and hence the nasal airway, of the subject. By providing for the escape of exhaled air from the exhalation breath of a subject through the nostril of the subject when the nosepiece 40 is not sufficiently inserted in the nostril of the subject for effective operation of the delivery device, the pressure which can be developed in the chamber 34 in the housing 32 by the subject is insufficient to actuate the delivery device, as will be described in more detail hereinbelow. When the nosepiece 40 is sufficiently inserted in a nostril of a subject for effective operation of the delivery device, the exhaled air from the exhalation breath of the subject has no means of escape other than through the nostril of the subject, and thereby allows for actuation of the delivery device on generation of a predetermined actuation pressure within the chamber 34 in the housing 32.

The delivery device further comprises a nozzle 56 for providing an aerosol through the nosepiece 40. The nozzle 56 comprises a head 58 which is located, in this embodiment co-axially, within the nosepiece 40, and a delivery tube 62 which is fluidly connected to the head 58. In an alternative embodiment the nozzle 56 could be configured to provide a jet of a substance through the nosepiece 40.

The delivery device further comprises a substance supply unit 64 for delivering a metered dose of a substance to the nozzle 56.

The substance supply unit 64 comprises a mechanical delivery pump 66 which is fluidly connected to the nozzle 56 and configured, on actuation thereof, to deliver a metered dose of a substance to the nozzle 56, which nozzle 56 generates an aerosol. The delivery pump 66 is movable relative to the nozzle 56 from a first, non-actuated position (as illustrated in FIGS. 2(*a*) to (*c*)) to a second, actuated position (as illustrated in FIG. 2(*d*)) to deliver a metered dose of a substance to the nozzle 56, and hence generate an aerosol.

In this embodiment the mechanical delivery pump 66 comprises a liquid delivery pump for delivering a metered volume of a liquid, here a liquid containing a medicament, either as a suspension or solution, to the nozzle 56 on actuation thereof.

In an alternative embodiment the mechanical delivery pump 66 could comprise a powder delivery pump for delivering a metered amount of a powder, here a powder containing a medicament, to the nozzle 56 on actuation thereof.

The substance supply unit 64 further comprises a biasing element 68, in this embodiment a resilient element, particularly a compression spring, for biasing the delivery pump 66 in an actuating direction when in the non-actuated position, and a loading mechanism 70, in this embodiment comprising first and second levers, for loading the biasing element 68 such as to bias the delivery pump 66, when in the non-actuated position, with an actuation force. The loading mechanism 70 is movable between a first, rest position in which the biasing element 68 is not loaded thereby, and a second, operative position in which the biasing element 68, when restrained by the delivery pump 66, loads the delivery pump 66 with the actuation force.

The delivery device further comprises a trigger mechanism 74 which is configured to be actuatable to cause the actuation of the substance supply unit 64. In this embodiment the trigger mechanism 74 is configured to be actuatable to cause the actuation of the substance supply unit 64 on the generation of a predetermined pressure in the chamber 34 in the housing 32. In an alternative embodiment the trigger mechanism 74 could be configured to be actuatable to cause the actuation of the substance supply unit 64 on the generation of a predetermined flow rate through the mouthpiece 42.

The trigger mechanism 74 comprises first and second stop members 76, 78, and first and second biasing elements 80, 82, in this embodiment resilient elements, particularly compression springs, which act to bias respective ones of the first and second stop members 76, 78 inwardly to a stop position (as illustrated in FIGS. 2(*a*) to (*c*)) in which the first and second stop members 76, 78 act to prevent movement of the delivery pump 66 from the non-actuated position to the actuated position.

The trigger mechanism 74 further comprises first and second arms 86, 88 which are pivotable about respective pivots 90, 92 and coupled at one end thereof to respective ones of the first and second stop members 76, 78 such that pivoting of the arms 86, 88 to a release position causes the respective ones of the stop members 76, 78 to which the arms 86, 88 are coupled to be moved outwardly against the bias of the first and second biasing elements 80, 82 to a release position (as illustrated in FIG. 2(*d*)) in which the stop members 76, 78 are disposed outwardly of the head of the delivery pump 66, such that the delivery pump 66, when biased by the biasing element 68, is driven to the actuated position. In being driven to the actuated position, a metered dose of a substance is delivered from the delivery pump 66 to the nozzle 56, with the nozzle 56 acting to generate an aerosol.

The trigger mechanism 74 further comprises a diaphragm 96, in this embodiment a resilient member, which defines a part of the wall of the chamber 34 in the housing 32.

The diaphragm 96 is configured such as, on generation of a predetermined actuation pressure within the chamber 34 in the housing 32, to be deflected such as to engage the other, distal ends of the arms 86, 88 and cause the same to be pivoted to the release position. This actuation pressure cannot be achieved until the nosepiece 40 is sufficiently inserted in a nostril of a subject for effective operation of the delivery device, in which position the escape of exhaled air from the exhalation breath of the subject directly to the atmosphere is prevented. Whilst the nosepiece 40 is not sufficiently inserted into a nostril of a subject as to provide for effective operation of the delivery device, exhaled air from the exhalation breath of the subject escapes to the atmosphere, thereby preventing the development of the actuation pressure within the chamber 34 in the housing 32.

With this configuration, the delivery device, in being pre-primed and actuatable by the oral exhalation breath of a subject, does not require the application of an actuation force by the subject at the instance of actuation, and provides for the closure of the oropharyngeal velum of the subject. Traditionally, mechanical liquid delivery pumps are operated by the manual compression of a chamber containing a volume of liquid to expel a flow of a metered volume of liquid, and mechanical powder delivery pumps are operated by the manual compression of a chamber containing a volume of air to drive and expel a flow of a metered amount of a dry powder. Such operation requires a relatively high actuation force, typically of the order of 50 N, which high force often leads to significant movement of the nasal delivery device, it being very difficult to maintain a nasal delivery device stationary when attempting to apply a high actuation force. Movement of the delivery device, both in the positioning and orientation of the nozzle, will lead to poor reproducibility, dose accuracy and patient compliance. In being pre-primed and actuatable by the oral exhalation breath of a subject, the delivery device of the present invention overcomes this problem, and, in having two points of fixation, namely at the nosepiece 40 and the mouthpiece 42, positioning and orientation of the delivery device can be ensured. In addition, by not requiring a subject to apply an actuation force at the instance of actuation, the delivery device provides for the same actuation force in each delivery, and also provides for delivery at an optimal pressure and/or flow rate, and the delivery of substance having an optimized particle size distribution. Furthermore, in providing for the closure of the oropharyngeal velum of a subject, substance is prevented from entering the lower airway, and also, in a preferred embodiment, bi-directional delivery can be achieved through the nasal cavities.

FIGS. 3(a) to (d) illustrate an oral exhalation breath-actuated nasal delivery device in accordance with a second embodiment of the present invention.

The delivery device of this embodiment is very similar to the delivery device of the above-described first embodiment, and thus, in order to avoid unnecessary duplication of description, only the differences will be described in detail, with like reference signs designating like parts.

The delivery device of this embodiment differs from that of the above-described first embodiment in further comprising an oral exhalation breath-actuatable gas supply unit 98 for delivering a gas flow to the chamber 34 in the housing 32 in response to exhalation by a subject, and in that the mouthpiece 42 is in fluid communication with the gas supply unit 98 and not the chamber 34 in the housing 32, whereby a controlled gas flow is delivered to the chamber 34 in the housing 32, and hence the nasal airway of a subject, from the gas supply unit 98 in response to exhalation through the mouthpiece 42.

Operation of the delivery device is the same as for the above-described first embodiment, with a gas flow being delivered to the chamber 34 in the housing 32, and hence a gas flow being developed in the nasal airway, by the gas supply unit 98 in response to exhalation through the mouthpiece 42.

Figure 4:
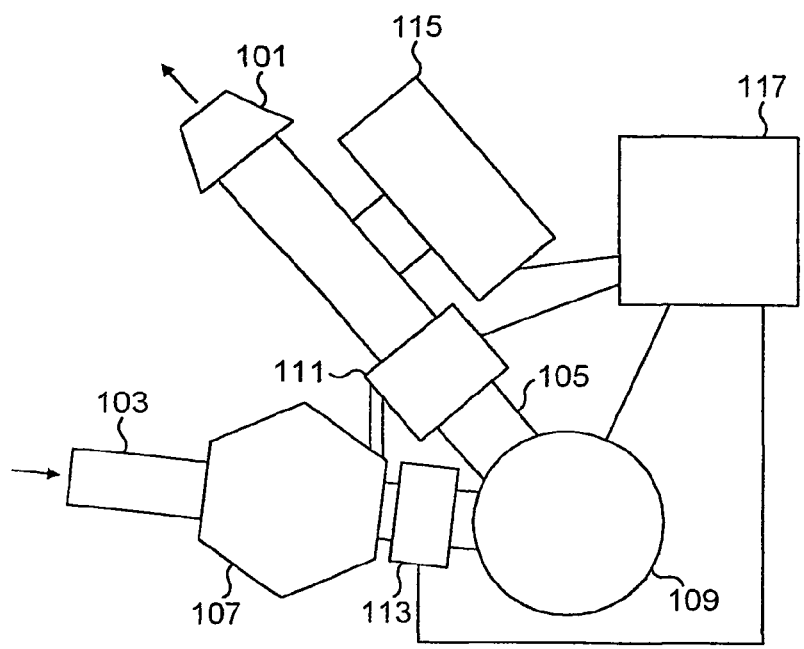
FIG. 4 illustrates an exhalation breath-actuated nasal delivery device in accordance with a third embodiment of the present invention.

FIG. 4 illustrates an oral exhalation breath-actuated nasal delivery device in accordance with a third embodiment of the present invention.

The delivery device comprises a nosepiece 101 for fitting in one nostril of a subject to provide a fluid-tight seal therewith, a mouthpiece 103 through which the subject exhales, and a flow channel 105 which fluidly connects the nosepiece 101 and the mouthpiece 103. With this configuration, exhaled air from an exhalation breath of a subject is delivered through the nasal airway of the subject.

In this embodiment the delivery device further comprises a filter unit 107 which is disposed at the inlet end of the flow channel 105, here including a moisture filter. In a preferred embodiment the filter unit 107 could include an anti-microbial filter.

The delivery device further comprises a pressure detector 109, in this embodiment an electronic pressure detector, which is disposed in the flow channel 105, in this embodiment downstream of the filter unit 107, for detecting the pressure developed in the flow channel 105 on exhalation therethrough by the subject.

The delivery device further comprises a flow meter 111, in this embodiment an electronic flow meter, which is disposed in the flow channel 105, in this embodiment downstream of the filter unit 107, for detecting the flow rate in the flow channel 105 on exhalation therethrough by the subject.

The delivery device further comprises a flow regulator 113 which is disposed upstream of the pressure sensor 109 and actuatable to control the flow rate of the exhaled air flow. In this embodiment the flow regulator 113 includes an electrically-operable baffle which is movable, in the flow channel 105 to restrict the flow therethrough and thereby enable control of the flow rate to predeterminable values.

The delivery device further comprises a nebulizer 115 which is in fluid communication with the flow channel 105, in this embodiment upstream of the flow meter 111, and actuatable to deliver a metered dose of a substance as an aerosol.

In this embodiment the nebulizer 115 comprises an ultrasonic nebulizer, whereby a liquid aerosol is generated by the vibration of a liquid supply, here a liquid containing a medicament, either as a solution or suspension, at a predetermined frequency, typically utilizing a piezo-electric element, with the frequency determining the particle size distribution of the delivered aerosol.

In another embodiment the nebulizer 115 could comprise a flow-induced nebulizer, whereby a gas flow interacts with a liquid supplied from a nozzle to generate a liquid aerosol, with the flow rate and the nozzle geometry determining the particle size distribution of the delivered aerosol.

In a further embodiment the nebulizer 115 could comprise an electrohydrodynamic (EHD) nebulizer, such nebulizers being capable of generating aerosols from liquid solutions or suspensions. In this nebulizer, flows of liquid are charged by an electric field, which charge builds up on the liquid surface, such that, when the liquid flows exit the respective nozzles, the repelling force of the surface charge overcomes the surface tension of the liquid and develops a fine aerosol. The particle size distribution of the aerosol can be controlled by adjusting a number of variables, such as physical and chemical properties of the drug formulations, the operating conditions and the electric field.

The delivery device further comprises a control unit 117 which is operably coupled to the pressure sensor 109, the flow meter 111, the flow regulator 113 and the nebulizer 115. The control unit 117 is configured to monitor the pressure detected by the pressure sensor 109 and the flow rate detected by the flow meter 111, and actuate the nebulizer 115 on the establishment of one or both of a predetermined pressure at and a predetermined flow rate through the flow channel 105, thereby providing for optimal delivery of substance to the nasal airway of a subject.

Operation of the delivery device will now be described hereinbelow.

A subject fits the nosepiece 101 to one nostril and grips the mouthpiece 103 in the mouth. The subject then exhales through the mouthpiece 103 such as to deliver the air flow from an exhalation breath through the flow channel 105 and the nasal airway of the subject, in this embodiment a bi-directional air flow through the nasal cavities of the nasal airway, with the exhaled air flow first being filtered by the filter unit 107. The control unit 117 monitors the pressure detected by the pressure sensor 109 and the flow rate detected by the flow meter 111, and actuates the nebulizer 115 on the establishment of one or both of a predetermined pressure at and a predetermined flow rate through the flow channel 105, thereby providing for optimal delivery of the substance to the nasal airway.

Figure 5:
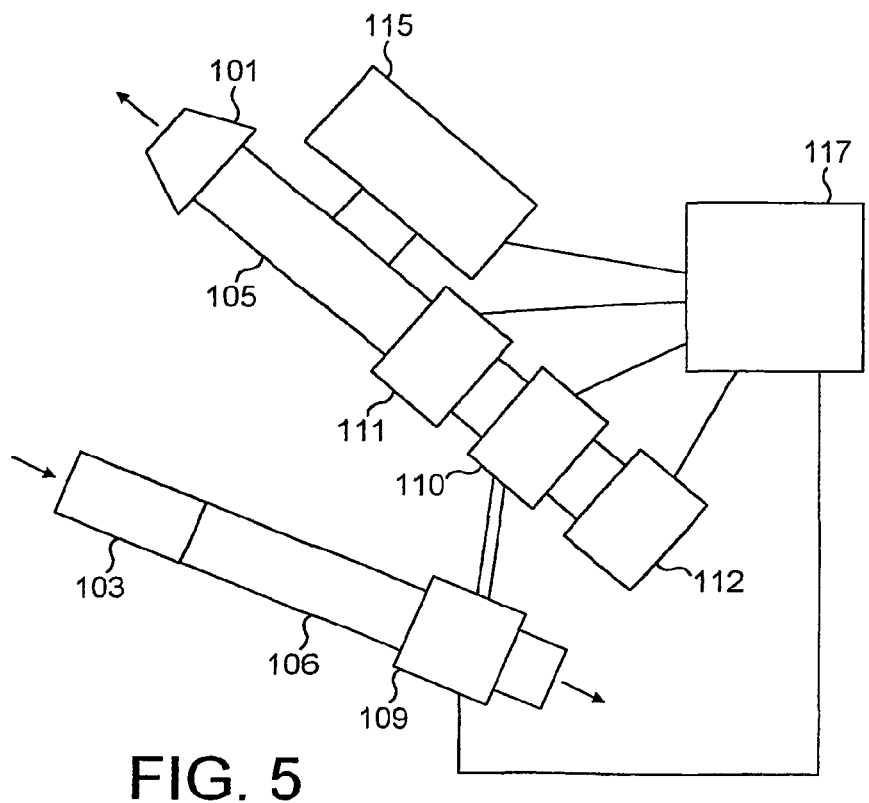
FIG. 5 illustrates an exhalation breath-actuated nasal delivery device in accordance with a fourth embodiment of the present invention.

FIG. 5 illustrates an oral exhalation breath-actuated nasal delivery device in accordance with a fourth embodiment of the present invention.

The delivery device comprises a nosepiece 101 for fitting in one nostril of a subject to provide a fluid-tight seal therewith, a mouthpiece 103 through which the subject exhales, a first flow channel 105 which is fluidly connected to the nosepiece 101, and a second flow channel 106 which is fluidly connected to the mouthpiece 103.

The delivery device further comprises a first pressure detector 109, in this embodiment an electronic pressure detector, which is disposed in the second flow channel 106 for detecting the generation of a predetermined pressure in the second flow channel 106 on exhalation by the subject therethrough; this pressure being indicative of the maintenance of an exhalation flow which is such as to maintain the oropharyngeal velum in the closed position, as is necessary for a bi-directional flow through the nasal cavities of a subject.

The delivery device further comprises a second pressure detector 110, in this embodiment an electronic pressure detector, which is disposed in the first flow channel 105 for detecting the pressure therein.

The delivery device further comprises a flow meter 111, in this embodiment an electronic flow meter, which is disposed in the first flow channel 105, in this embodiment downstream of the second pressure detector 110, for detecting the flow rate in the first flow channel 105.

The delivery device further comprises a regulatable gas supply unit 112 which is fluidly connected to the first flow channel 105, in this embodiment upstream of the second pressure detector 110, for delivering a controlled gas flow through the first flow channel 105, and hence the nasal airway of a subject.

The delivery device further comprises a nebulizer 115 which is in fluid communication with the first flow channel 105, in this embodiment downstream of the flow meter 111, and actuatable to deliver a metered dose of a substance.

In this embodiment the nebulizer 15 comprises an ultrasonic nebulizer, whereby a liquid aerosol is generated by the vibration of a liquid supply, here a liquid containing a medicament, either as a solution or suspension, at a predetermined frequency, typically utilizing a piezo-electric element, with the frequency determining the particle size distribution of the delivered aerosol.

In another embodiment the nebulizer 115 could comprise a flow-induced nebulizer, whereby a gas flow interacts with a liquid supplied from a nozzle to generate a liquid aerosol, with the flow rate and the nozzle geometry determining the particle size distribution of the delivered aerosol.

In a further embodiment the nebulizer 115 could comprise an electrohydrodynamic (EHD) nebulizer, such nebulizers being capable of generating aerosols from liquid solutions or suspensions. In this nebulizer, flows of liquid are charged by an electric field, which charge builds up on the liquid surface, such that, when the liquid flows exit the respective nozzles, the repelling force of the surface charge overcomes the surface tension of the liquid and develops a fine aerosol. The particle size distribution of the aerosol can be controlled by adjusting a number of variables, such as physical and chemical properties of the drug formulations, the operating conditions and the electric field.

The delivery device further comprises a control unit 117 which is operably coupled to the first and second pressure sensors 109, 110, the flow meter 111, the regulatable gas supply unit 112 and the nebulizer 115. The control unit 117 is configured to monitor the pressure detected by the second pressure sensor 110 and the flow rate detected by the flow meter 111, and actuate the nebulizer 115 on the establishment of one or both of a predetermined pressure at and a predetermined flow rate through the first flow channel 105, thereby providing for optimal delivery of a substance to the nasal airway of a subject. In this embodiment the control unit 117 is configured to enable actuation of the gas supply unit 112 and the nebulizer 115 only on detection of a predetermined pressure by the first pressure sensor 109; this pressure being indicative that the subject is exhaling through the mouthpiece 103 with sufficient force as to close the oropharyngeal velum of the subject, and thereby prevent delivery to the lower airway and ensure bi-directional delivery through the nasal cavities of the subject.

Operation of the delivery device will now be described hereinbelow.

A subject fits the nosepiece 101 to one nostril and grips the mouthpiece 103 in the mouth.

The subject then exhales through the mouthpiece 103, which exhalation is such as to cause closure of the oropharyngeal velum of the subject. On detection of a predetermined pressure by the first pressure sensor 109, the control unit 117 actuates the gas supply unit 112 to deliver a gas flow having a predetermined flow rate such as to deliver a gas flow through the first flow channel 105 and the nasal airway of the subject, in this embodiment a bi-directional air flow through the nasal cavities of the nasal airway. The control unit 117 monitors the pressure detected by the second pressure sensor 110 and the flow rate detected by the flow meter 111, and actuates the nebulizer 115 on the establishment of one or both of a predetermined pressure at and a predetermined flow rate through the first flow channel 105, thereby providing for optimal delivery of a substance to the nasal airway.

Finally, it will be understood that the present invention has been described in its preferred embodiments and can be modified in many different ways without departing from the scope of the claimed invention as defined by the appended claims.

For example, it will be understood that the present invention finds application in multi-dose or single-dose delivery devices, in particular multi-dose and single-dose delivery pumps.

What is claimed is:

1. An exhalation breath-actuated nasal delivery device for delivering a substance to a nasal cavity of a subject, comprising:
   a nosepiece for filling to a nostril of a subject;
   a mouthpiece through which the subject in use exhales;
   a nozzle for directing a substance through the nosepiece;
   a mechanical delivery pump fluidly connected to the nozzle for delivering a substance to the nozzle; and
   an actuation mechanism for actuating the mechanical delivery pump in response to oral exhalation through the mouthpiece.

2. The delivery device of claim 1, wherein the actuation mechanism includes a trigger mechanism for actuating the delivery pump at a predeterminable pressure.

3. The delivery device of claim 1, wherein the actuation mechanism includes a trigger mechanism for actuating the delivery pump at a predeterminable flow rate.

4. The delivery device of claim 1, wherein the actuation mechanism includes a trigger mechanism for actuating the delivery pump at one or both of a predeterminable pressure and a predeterminabie flow rate.

5. The delivery device of claim 1, further comprising:
   a flow channel fluidly connecting the nosepiece and the mouthpiece, whereby exhaled air from an exhalation breath is in use delivered through the nosepiece.

6. The delivery device of claim 1, further comprising:
   a flow channel fluidly connected to the nosepiece through which a gas flow, separate to an exhaled air flow from an exhalation breath of the subject, is in use delivered; and
   a gas supply unit for supplying a gas flow to the flow channel.

7. The delivery device of claim 6, wherein the gas supply unit is configured to be actuated by exhalation through the mouthpiece.

8. The delivery device of claim 1, wherein the delivery pump comprises a liquid delivery pump for delivering a metered volume of a liquid.

9. The delivery device of claim 1, wherein the delivery pump comprises a powder delivery pump for delivering a metered amount of a powder.

10. The delivery device of claim 1, wherein the nozzle is configured to deliver an aerosol.

11. The delivery device of claim 1, wherein the nozzle is configured to deliver a jet.

12. A method of delivering a substance to a nasal cavity of a subject, comprising the steps of:
providing a nasal delivery device to the nasal cavity of a subject, the delivery device including a nosepiece for filling to a nostril of the subject, a mouthpiece through which the subject exhales, a nozzle for directing a substance through the nosepiece, and a mechanical delivery pump fluidly connected to the nozzle for delivering a substance to the nozzle; and
actuating the delivery pump in response to oral exhalation through the mouthpiece to deliver a substance through the nosepiece.

13. The method of claim 12, wherein the step of actuating the delivery pump comprises the step of:
actuating the delivery pump in response to oral exhalation through the mouthpiece on generation of a predeterminable pressure at the nosepiece.

14. The method of claim 12, wherein the step of actuating the delivery pump comprises the step of:
actuating the delivery pump in response to oral exhalation through the mouthpiece on generation of a predeterminable flow rate through the nosepiece.

15. The method of claim 12, wherein the step of actuating the delivery pump comprises the step of:
actuating the delivery pump in response to oral exhalation through the mouthpiece on generation of one or both of a predeterminable pressure at or a predeterminable flow rate through the nosepiece.

16. The method of claim 12, wherein:
the delivery device further comprises a flow channel fluidly connecting the nosepiece and the mouthpiece, whereby exhaled air from an exhalation breath is delivered through the nosepiece.

17. The method of claim 12, further comprising the step of:
delivering a gas flow, separate to an exhaled air flow from an exhalation breath of the subject, through the nosepiece.

18. The method of claim 12, wherein the delivery pump comprises a liquid delivery pump for delivering a metered volume of a liquid.

19. The method of claim 12, wherein the delivery pump comprises a powder delivery pump for delivering a metered amount of a powder.

20. The method of claim 12, wherein the substance is delivered as an aerosol.

21. The method of claim 12, wherein the substance is delivered as a jet.

22. An exhalation breath-actuated nasal delivery device for delivering a substance to a nasal cavity of a subject, comprising:
a nosepiece for fitting to a nostril of a subject;
a mouthpiece through which the subject in use exhales;
a nebulizer for delivering an aerosol including a substance to the nosepiece; and
an actuation unit for actuating the nebulizer when at least one or both of the pressure at or the flow rate through the nosepiece exceeds a predetermined threshold in response to oral exhalation through the mouthpiece.

23. The delivery device of claim 22, further comprising:
a flow channel fluidly connecting the nosepiece and the mouthpiece, whereby exhaled air from an exhalation breath is in use delivered through the nosepiece.

24. The delivery device of claim 23, wherein the actuation unit includes a flow regulator for regulating a flow of exhaled air from an exhalation breath.

25. The delivery device of claim 22, further comprising:
a flow channel fluidly connected to the nosepiece through which a gas flow, separate to an exhaled air flow from an exhalation breath of the subject, is in use delivered; and
a gas supply unit for supplying a gas flow to the flow channel.

26. The delivery device of claim 25, wherein the gas supply unit is configured to be actuated by exhalation through the mouthpiece.

27. The delivery device of claim 22, wherein the nebulizer comprises an ultrasonic nebulizer.

28. The delivery device of claim 22, wherein the nebulizer comprises a flow-generated nebulizer.

29. The delivery device of claim 22, wherein the nebulizer comprises an electrohydrodynamic nebulizer.

30. A method of delivering a substance to a nasal cavity of a subject, comprising the steps of:
providing a nasal delivery device comprising a nosepiece for fitting to a nostril of a subject, a mouthpiece through which the subject exhales, and a nebulizer for delivering an aerosol including a substance to the nosepiece; and
actuating the nebulizer when at least one or both of the pressure at or the flow rate through the nosepiece exceeds a predetermined threshold in response to oral exhalation through the mouthpiece.

31. The method of claim 30, wherein:
the delivery device further comprises a flow channel fluidly connecting the nosepiece and the mouthpiece, whereby exhaled air from an exhalation breath is delivered through the nosepiece.

32. The method of claim 31, wherein:
the delivery device further comprises a flow regulator for regulating a flow of exhaled air from an exhalation breath.

33. The method of claim 30, further comprising the step of:
delivering a gas flow, separate to an exhaled air flow from an exhalation breath of the subject, through the nosepiece.

34. The method of claim 30, wherein the nebulizer comprises an ultrasonic nebulizer.

35. The method of claim 30, wherein the nebulizer comprises a flow-generated nebulizer.

36. The method of claim 30, wherein the nebulizer comprises an electrohydrodynamic nebulizer.

* * * * *